(12) United States Patent
Ghasr et al.

(10) Patent No.: US 9,482,626 B2
(45) Date of Patent: Nov. 1, 2016

(54) WAVEGUIDE PROBE FOR NONDESTRUCTIVE MATERIAL CHARACTERIZATION

(71) Applicant: The Curators of the University of Missouri, Columbia, MO (US)

(72) Inventors: Mohammad Tayeb Ghasr, Rolla, MO (US); Matthew Kempin, Overland Park, KS (US); Reza Zoughi, Wildwood, MO (US)

(73) Assignee: The Curators of the University of Missouri, Columbia, MO (US)

( * ) Notice: Subject to any disclaimer, the term of this patent is extended or adjusted under 35 U.S.C. 154(b) by 464 days.

(21) Appl. No.: 14/026,754

(22) Filed: Sep. 13, 2013

(65) Prior Publication Data

US 2015/0077138 A1 Mar. 19, 2015

(51) Int. Cl.
*G01R 27/32* (2006.01)
*G01R 27/04* (2006.01)
*G01N 22/00* (2006.01)
*G01N 22/02* (2006.01)

(52) U.S. Cl.
CPC .............. *G01N 22/00* (2013.01); *G01N 22/02* (2013.01)

(58) Field of Classification Search
CPC .............................. G01N 22/00; G01N 22/02
USPC .................................................. 324/637, 642
See application file for complete search history.

(56) References Cited

U.S. PATENT DOCUMENTS

| 5,233,306 | A | 8/1993 | Misra |
| 5,748,003 | A | 5/1998 | Zoughi et al. |
| 5,781,018 | A * | 7/1998 | Davidov et al. .............. 324/637 |
| 2007/0205936 | A1 | 9/2007 | McMakin et al. |
| 2010/0033709 | A1 | 2/2010 | Lampin et al. |
| 2010/0109932 | A1 | 5/2010 | Liu |
| 2010/0176789 | A1 | 7/2010 | Zoughi et al. |
| 2010/0204581 | A1 | 8/2010 | Chalana et al. |
| 2013/0225989 | A1 | 8/2013 | Saroka et al. |

FOREIGN PATENT DOCUMENTS

WO 2009/078814 A1 6/2009

OTHER PUBLICATIONS

Baker-Jarvis, J., et al., "Transmission/Reflection and Short-Circuit Line Method for Measuring Permittivity and Permeability," NIST Tech. Note 1355-R, U.S. Dept. Commerce, Boulder, CO, pp. 52-57, Dec. 1993.

(Continued)

*Primary Examiner* — Amy He
(74) *Attorney, Agent, or Firm* — Senniger Powers LLP

(57) ABSTRACT

An open-ended waveguide probe including a finite flange extending outwardly and functioning as an infinite flange. A signal source provides a microwave signal to the waveguide, which in turn transmits microwave electromagnetic energy incident upon an object to be tested. The finite flange at the waveguide's aperture is shaped to reduce scattering of the electromagnetic field reflected from the object and received by the aperture. The probe is adapted for coupling to a receiver for sampling the reflected electromagnetic field received by the aperture and the receiver is adapted for coupling to a processor for determining at least one material characteristic of the object based on sampled electromagnetic field reflected from the object.

26 Claims, 11 Drawing Sheets

(56) References Cited

OTHER PUBLICATIONS

Bakhtiari, S., et al., "Open-Ended Rectangular Waveguide for Nondestructive Thickness Measurement and Variation Detection of Lossy Dielectric Slabs Backed by a Conducting Plate," IEEE Transactions on Instrumentation and Measurement, vol. 42, No. 1, pp. 19-24, Feb. 1993.

Bois, K. J., et al., "Dielectric Plug-Loaded Two-Port Transmission Line Measurement Technique for Dielectric Property Characterization of Granular and Liquid Materials," IEEE Transactions on Instrumentation and Measurement, vol. 48, No. 6, pp. 1141-1148, Dec. 1999.

Bois, K. J., et al., "Multimode Solution for the Reflection Properties of an Open-Ended Rectangular Waveguide Radiating into a Dielectric Half-Space: The Forward and Inverse Problems." IEEE Transactions on Instrumentation and Measurement, vol. 48, No. 6, pp. 1131-1140, Dec. 1999.

Chang, C. W., et al., "Nondestructive Determination of Electromagnetic Parameters of Dielectric Materials at X-band Frequencies Using a Waveguide Probe System," IEEE Transactions on Instrumentation and Measurement, vol. 46, No. 5, pp. 1084-1092, Oct. 1997.

CST—Computer Simulation Technology, http://www.cst.com, Feb. 19, 2014, 2 pgs.

Fallahpour, M., et al., "Simultaneous Evaluation of Multiple Key Material Properties of Complex Stratified Structures with Large Spatial Extent," in Review of Progress in Quantitative Nondesctructive Evaluation vol. 31A, Burlington, VT, Jul. 17-22, vol. 1430, AIP Conference Proceedings, edited by D.O. Thompson and D.E. Chimenti, American Institute of Physics, pp. 561-565 (2012).

Ghasr, M. T., et al., "Multimodal Solution for a Waveguide Radiating into Multilayered Structures—Dielectric Property and Thickness Evaluation," IEEE Transactions on Instrumentation and Measurement, vol. 58, No. 5, pp. 1505-1513, May 2009.

Kharkovsky, S. et al., "Near-Field Millimeter-Wave Imaging of Exposed and Covered Fatigue Cracks," IEEE Transactions on Instrumentation and Measurement, vol. 58, No. 7, pp. 2367-2370, Jul. 2009.

Moade, N., et al., "An Improved Open-Ended Waveguide Measurement Technique on Parameters er and mr of High-Loss Materials," IEEE Transactions on Instrumentation and Measurement, vol. 47, No. 2, pp. 476-481, Apr. 1999.

Theodoris, V. et al., "The Reflection From an Open-Ended Rectangular Waveguide Terminated by a Layered Dielectric Medium," IEEE Transactions on Microwave Theory Techniques, vol. MTT-33, No. 5, pp. 359-366, May 1985.

Vanzura, E.J., et al., "Intercomparison of Permittivity Measurements Using the Transmission/Reflection Method in 7-mm Coaxial Transmission Lines" IEEE Transactions on Microwave Theory and Techniques, vol. 42, No. 11, pp. 2063-2070, Nov. 1994.

Williams, D. F., et al., "Legendre Fit to the Reflection Coefficient of a Radiating Rectangular Waveguide Aperture," IEEE Transactions on Antennas and Propagation, vol. 60, No. 8, pp. 4009-4014, Aug. 2012.

Yoshitomi, K. et al., "Radiation from a rectangular waveguide with a lossy flange," IEEE Transactions on Antennas and Propagation, vol. 42, No. 10, pp. 1398-1403, Oct. 1994.

Zoughi, R., Microwave Non-Destructive Testing and Evaluation, Kluwer Academic Publishers, The Netherlands, 2000, 6 pages.

* cited by examiner

WAVEGUIDE PROBE FOR NONDESTRUCTIVE MATERIAL CHARACTERIZATION

STATEMENT REGARDING FEDERALLY SPONSORED RESEARCH OR DEVELOPMENT

This invention was made with government support under Contract No. FA8117-12-C-0004 awarded by the Department of Defense. The government has certain rights in the invention.

BACKGROUND

Open-ended rectangular waveguide probes have demonstrated utility for many applications in the field of microwave and millimeter-wave nondestructive testing and evaluation. Such testing and evaluation includes three-dimensional imaging, crack detection, and material characterization. In many instances, using an open-ended rectangular waveguide for material characterization is preferred over other techniques such as loaded transmission line or cavity techniques that require the material being tested to be cut and shaped to fit inside the transmission line or cavity.

FIG. 1 illustrates a probe 100 for use in determining electrical and magnetic (complex dielectric and permeability) properties of materials. The probe 100 comprises an open-ended waveguide 102 having a finite flange 106. In operation, a signal source provides a microwave signal to the waveguide, which in turn transmits microwave electromagnetic energy incident upon an object to be tested. The microwave electromagnetic energy penetrates the object placed in front of the open end of the waveguide based on the object's dielectric properties. Cracks and other surface variations affect the dielectric properties and are thus detectable by the probe.

When used for material characterization, conventional open-ended rectangular waveguide probes, such as the probe 100, require robust full-wave electromagnetic models along with optimization algorithms to achieve acceptable accuracies. Such electromagnetic models provide the reflection coefficient at the aperture of the waveguide radiating into a dielectric structure. But any small error in modeling and/or measurement of the reflection coefficient may lead to unacceptable errors in estimating the dielectric constant or thickness when measuring the dielectric properties and thicknesses of thin and low loss materials, especially when they are embedded within a structure containing thicker and lossy dielectrics.

Even if an electromagnetic model accounts for generated higher-order modes and is generally accurate, the finite flange 106 contributes to the majority of the error in estimating the dielectric constant and/or thickness of a layer or layers within a stratified dielectric composite structure. This is due to the fact that the model assumes an infinite flange, while measurements are commonly conducted using waveguides with standard finite flanges. Moreover, through extensive measurements it has been shown that the adverse effect of the finite flange 106 is more significant for estimating the dielectric constant or thickness, especially for thin and low permittivity and low loss materials. This adverse effect has further significance for conductor-backed composite structures.

Consequently, when performing measurements using a conventional open-ended rectangular waveguide, a very large flange is sometimes used. Otherwise, testing must be limited to primarily lossy materials or else the errors introduced by flange 102 cause poor measurements. In other words, accurate measurements of low loss material characteristics cannot be taken by a conventional open-ended rectangular waveguide such as probe 100. Although a lossy dielectric sheet may be used as a coupling medium to reduce the flange effect, the extra attenuation introduced by this additional lossy sheet reduces the measurement sensitivity.

SUMMARY

Aspects of the invention help mitigate the effects of edge reflections from a finite flange. By modifying the flange geometry, aspects of the invention permit improved accuracy of material (and geometrical) characterization when using relative permittivity and loss tangent calculations.

Briefly described, an open-ended waveguide apparatus embodying aspects of the invention includes a hollow guiding structure and a signal source coupled to it. The guide structure further has an open end that defines an aperture through which an electromagnetic signal generated by the signal source is transmitted to an object located remotely from the aperture. In addition, an electromagnetic field reflected from the object is received by the aperture. The apparatus also includes a flange at the aperture. Two or more of the flange edges are shaped to reduce unwanted scattering of the electromagnetic field by these edges. The guide structure is adapted for coupling to a receiver for sampling the reflected electromagnetic field received by the aperture and the receiver is adapted for coupling to a processor for determining at least one material characteristic of the object based on sampled electromagnetic field reflected from the object.

In an aspect, a method of measuring a material characteristic of an object includes defining a flange geometry for an antenna as a function of the material characteristic to be measured and transmitting, by the antenna, an electromagnetic signal that includes microwave electromagnetic energy incident upon the object. The method also includes receiving, by the antenna, an electromagnetic field reflected from the object. The antenna has a flange extending outward therefrom and is shaped according to the defined flange geometry to reduce scattering, by one or more edges of the flange, of the electromagnetic field received by the antenna. Further, the method includes determining the material characteristic of the object based on the received electromagnetic field.

In another aspect, a system for non-destructive testing includes an open-ended waveguide having a signal source coupled to it. The waveguide defines an aperture through which an electromagnetic signal generated by the signal source is transmitted to an object located remotely from the aperture and through which an electromagnetic field reflected from the object is received by the aperture. A flange shaped to reduce scattering, by one or more edges of the flange, of the electromagnetic field received by the aperture extends outwardly from the waveguide at the aperture. The system further includes a processor configured to execute an estimation algorithm for determining at least one material characteristic of the object as a function of the reflected electromagnetic field received by the aperture.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
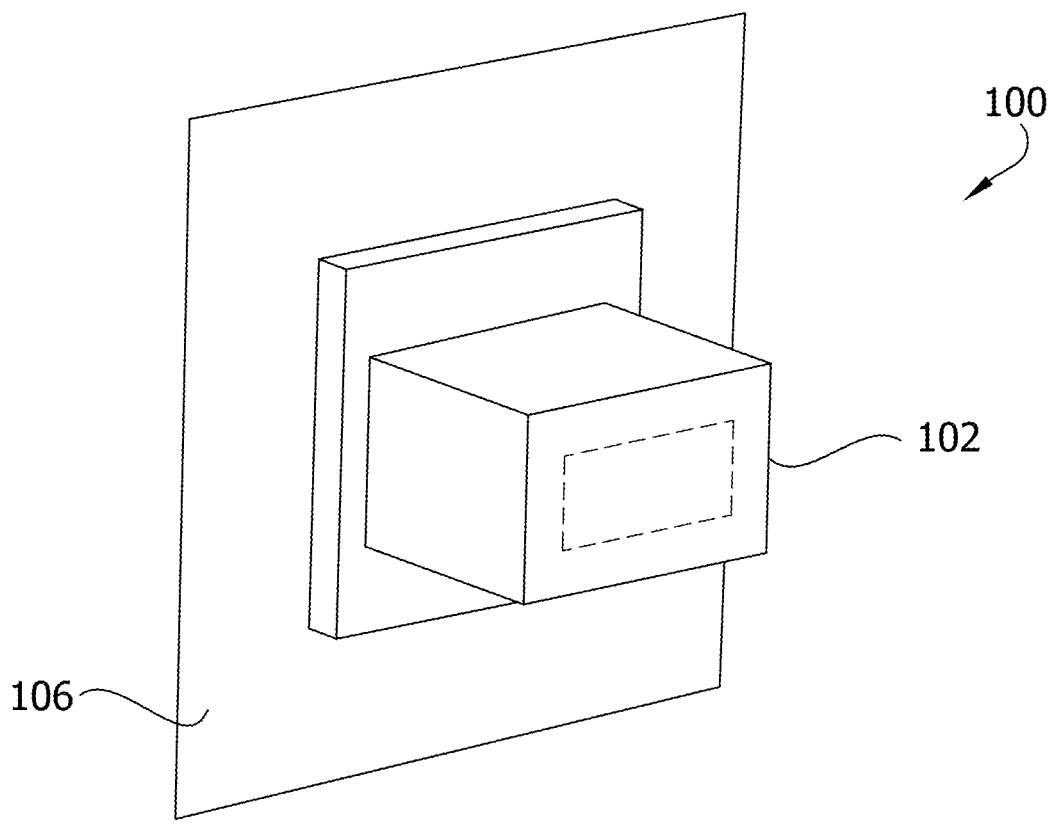
FIG. 1 illustrates an open-ended waveguide with a finite flange according to the prior art.

As described above, the probe 100 of FIG. 1 comprises open-ended waveguide 102 with finite flange 106. In operation, a signal source provides a microwave signal to the waveguide, which in turn transmits microwave electromagnetic energy incident upon an object to be tested. The microwave electromagnetic energy penetrates the object placed in front of the open end of the waveguide based on the object's dielectric properties. Variations in material characteristics, such as dielectric properties and thickness, are thus detectable by the probe.

Figure 2:
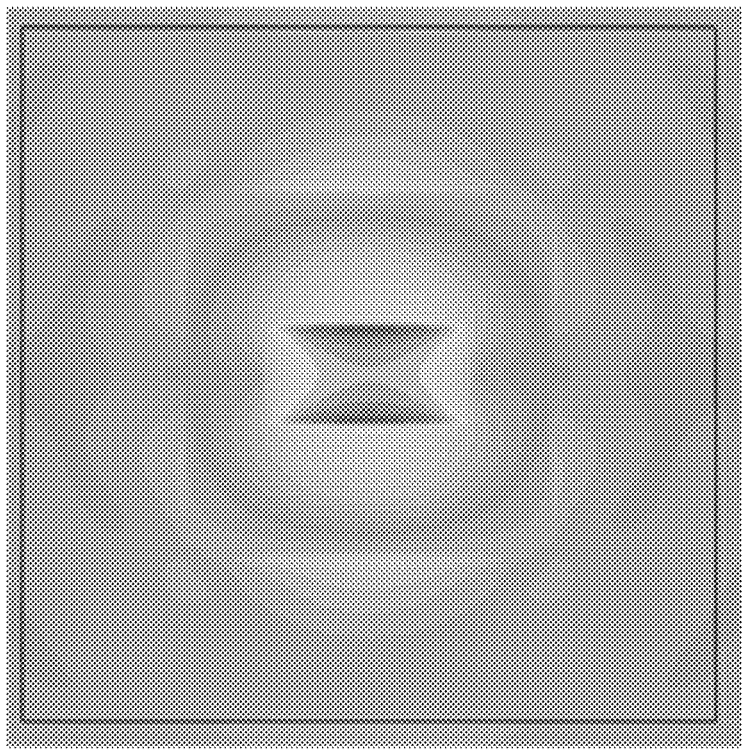
FIG. 2 illustrates exemplary electric field intensity inside a thin dielectric sheet into which the finite flange waveguide of FIG. 1 is radiating.

In use, the waveguide radiates into, for example, a thin sheet for measuring a material characteristic of the sheet. FIG. 2 illustrates exemplary electric field intensity (e.g., distribution) inside the thin dielectric sheet. As shown, the effect of the flange edge is to scatter or reflect some of the unwanted electric field back into the waveguide. The scattering of the electric field is stronger on the top and bottom edges of the flange 106 due to the preferred polarization of the electric field in the waveguide 102.

In addition, analysis of the effect of the finite flange 106 with respect to a vector reflection coefficient over the microwave and millimeter wave frequency bands, such as the X-band, reveals significant errors relative to ideal models (i.e., considering an infinite flange). The reflection coefficient for a relatively large sample (e.g., a dielectric sheet of 150 mm×150 mm×0.48 mm) differs from the reflection coefficient for a relatively small sample (e.g., a dielectric sheet of 75 mm×75 mm×0.48 mm). In general terms of mid-band wavelength, the reflection coefficient for a relatively large and thin sample (e.g., $5\lambda_0 \times 5\lambda_0 \times 0.016\lambda_0$, where $\lambda_0$ is the mid-band wavelength) differs from the reflection coefficient for a relatively small and thin sample (e.g., $2.5\lambda_0 \times 2.5\lambda_0 \times 0.016\lambda_0$). But compared to ideal models, the error in reflection coefficient due to the finite flange size is much larger than the error due to the finite sample size. Moreover, analysis shows that the effect of the sample size is minimal when the dielectric has more loss (e.g., lossy tan $\delta=0.1$ compared to lossy tan $\delta=0.01$). In other words, those skilled in the art will appreciate that finite flange 106 is a primary and significant source of error in microwave non-destructive testing.

Although various techniques may be employed for correcting or compensating for the effect of finite flange 106 on measurements, aspects of the present invention are more effective. One correction technique utilizes polynomial fitting to model the reflection coefficient of the waveguide 102. Undesirably, this polynomial fitting depends on the dielectric structure being tested. Therefore, for limited applications when a dielectric sheet is known, the polynomial fit may be implemented. But, in general, the polynomial fit correction is merely a mathematical correction and fails to reduce the scattering at the edge of flange 106 or to redirect the current density path on flange 106. In this manner, known corrections are not universally applicable and must be specifically adapted to particular measurement scenarios.

Figure 3:
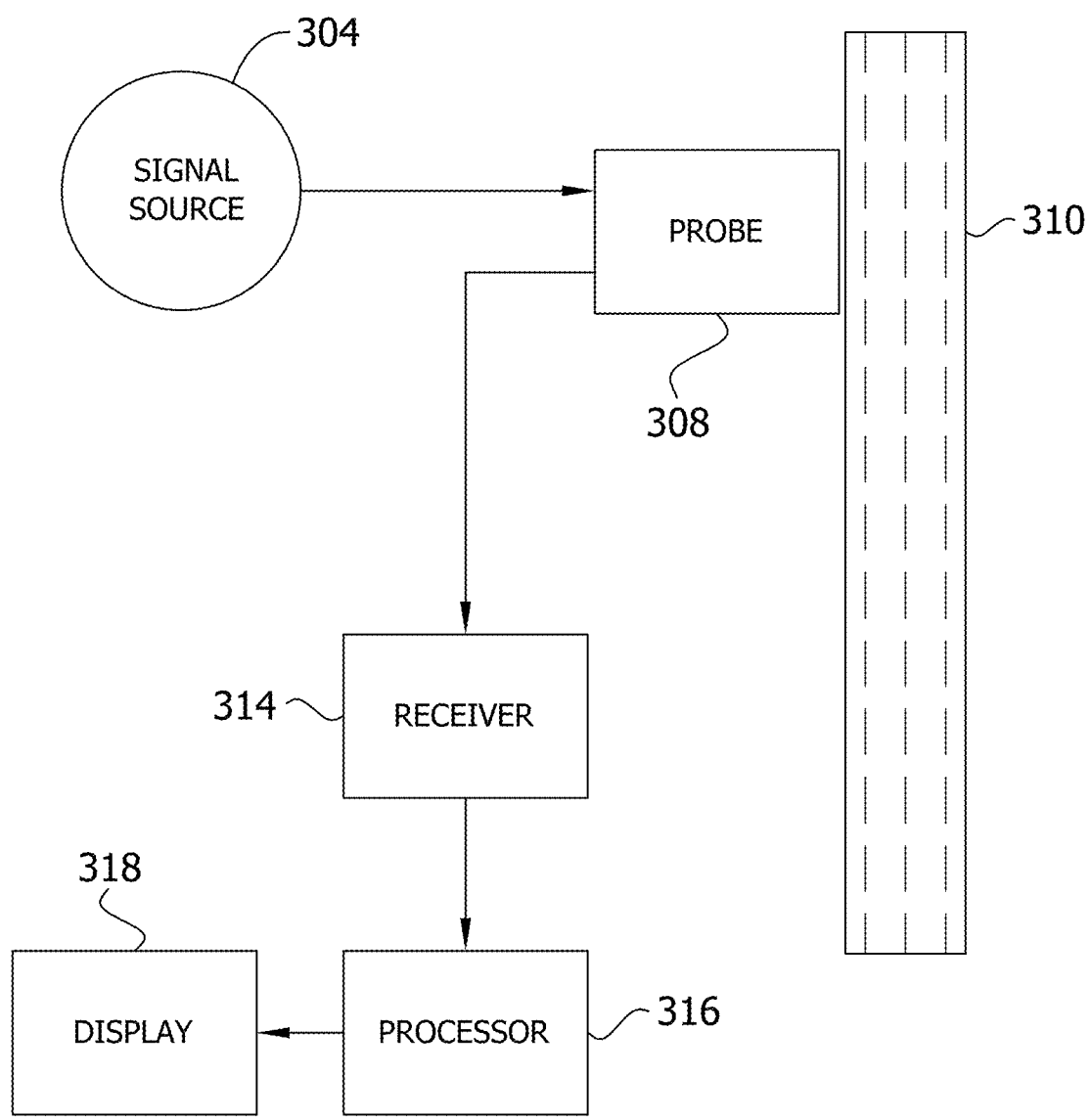
FIG. 3 is a block diagram of an exemplary test arrangement according to an embodiment of the invention.

FIG. 3 is a block diagram of an exemplary test arrangement according to an embodiment of the invention. A signal source 304 provides a microwave signal to a probe 308, which in turn transmits microwave electromagnetic energy incident upon an object 310 to be tested. In an embodiment, the signal source 304 comprises an electric field source for illuminating the object. The electric field comprises electromagnetic energy, such as microwave or millimeter wave electromagnetic energy, having a frequency greater than ultra high frequency and being reflected by the object illuminated thereby.

The microwave electromagnetic energy transmitted by probe 308 penetrates the object 310 placed in front of the open end of the waveguide based on the object's dielectric properties. In an embodiment, the object 310 is a thin dielectric sheet. In another embodiment, the object 310 comprises multiple layers.

In addition, an electromagnetic field reflected from object 310 is received by probe 308. The probe 308 is adapted for coupling to a receiver 314 for sampling the reflected electromagnetic field received by the probe. The receiver 314 is adapted for coupling to a processor 316 for determining at least one material characteristic of object 310 based on sampled electromagnetic field reflected from the object. In one embodiment, the processor 316 executes an estimation algorithm for determining the at least one material characteristic of the object as a function of the reflected electromagnetic field received by the aperture. For example, the material characteristic is a thickness, a complex permeability, and/or a complex dielectric constant.

In another embodiment, processor 316 is configured to generate a multi-dimensional profile representative of the object as a function of the reflected electromagnetic field and further comprises a display 318 operatively connected to the processor for displaying an image of the multi-dimensional profile generated thereby. The multi-dimensional profile comprises, for example, at least two of a complex dielectric constant of the object, a permeability of the object, and a thickness of the object.

Figure 4:
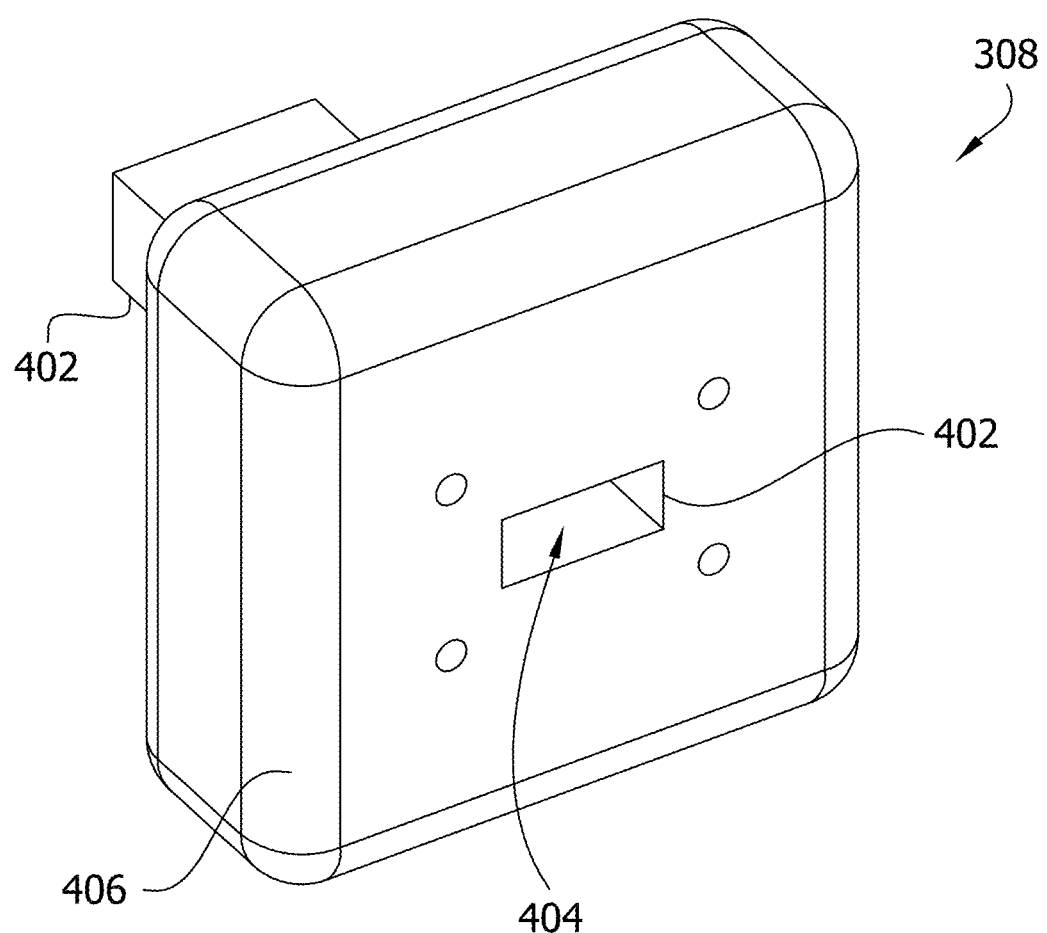
FIG. 4 illustrates an open-ended waveguide apparatus with a finite flange for use in the test arrangement of FIG. 3.

Referring now to FIG. 4, the probe 308 comprises an open-ended hollow guide structure 402 having an aperture 404. The guide structure 402 has an open end that defines the aperture 404 through which an electromagnetic signal generated by the signal source 304 is transmitted to object 310 located remotely from the aperture 404. As shown, the hollow guide structure 402 comprises a rectangular waveguide, that is, aperture 404 is substantially rectangular. But it is contemplated that aperture 404 can have a rectangular, square, circular, elliptical, or other cross-section. In use, the waveguide radiates electromagnetic energy from signal source 304 into, for example, a thin sheet (i.e., object 310) for measuring a material characteristic of the sheet. According to aspects of the invention, FIG. 4 illustrates an open-ended waveguide with a finite flange 406 for use in the test arrangement of FIG. 3.

In addition, an electromagnetic field reflected from object 310 is received by guide structure 402 via the aperture 404 and guide structure 402 is adapted for coupling to receiver 314 for sampling the reflected electromagnetic field received by aperture 404.

The flange 406 in this embodiment extends outward at aperture 404 (e.g., transversally). In an aspect of the invention, flange 406 as configured functionally approximates an infinite flange. The flange 406, which is constructed from or covered by, for example, a conductive metal, is shaped to reduce scattering of the electromagnetic field received by the aperture 404. As shown in this embodiment, flange 406 extends outwardly in three dimensions to functionally approximate an infinite flange. Any scattering caused by one or more of edges of flange 406 is significantly less than the scattering caused by finite flange 106 and, thus, a finite flange open-ended waveguide as shown in FIG. 4 provides improved accuracy.

Figure 5A:
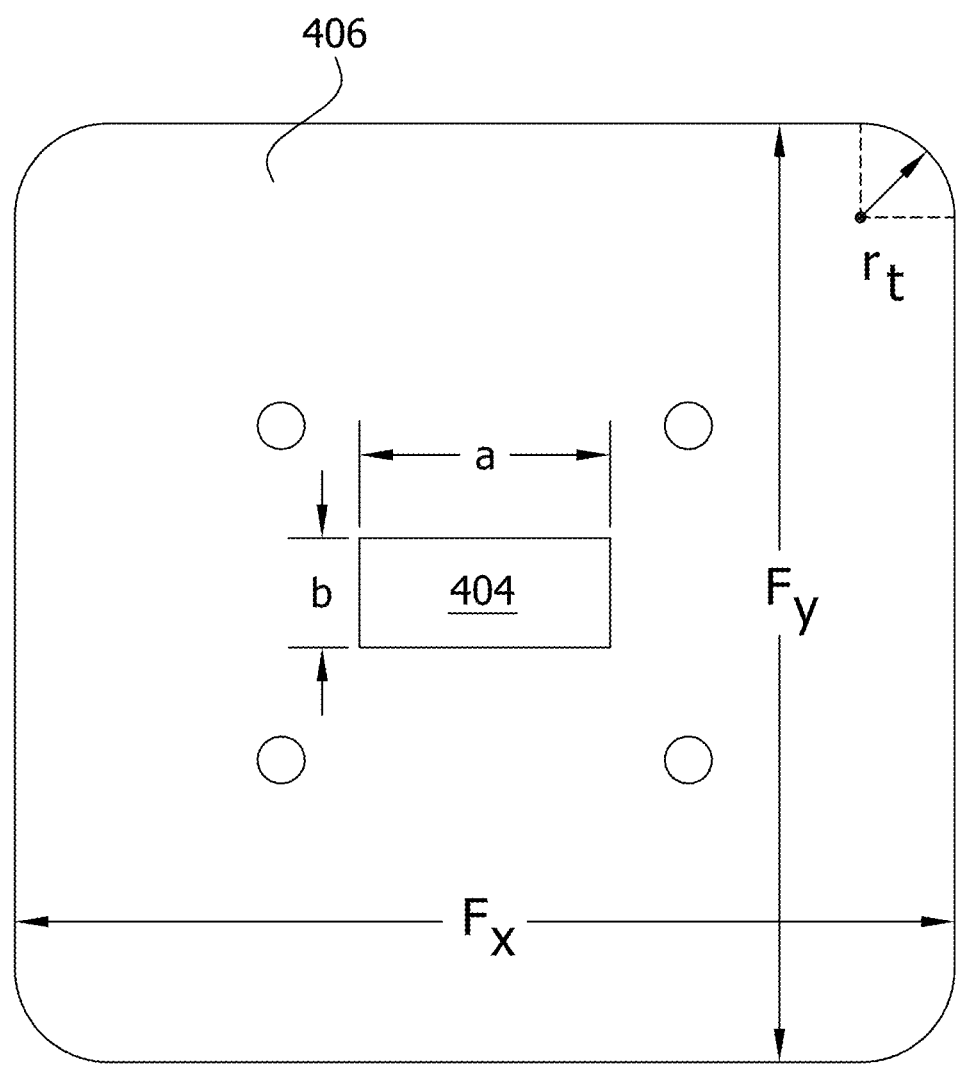
FIG. 5A is a plan view of the finite flange waveguide apparatus of FIG. 4.
Figure 5B:
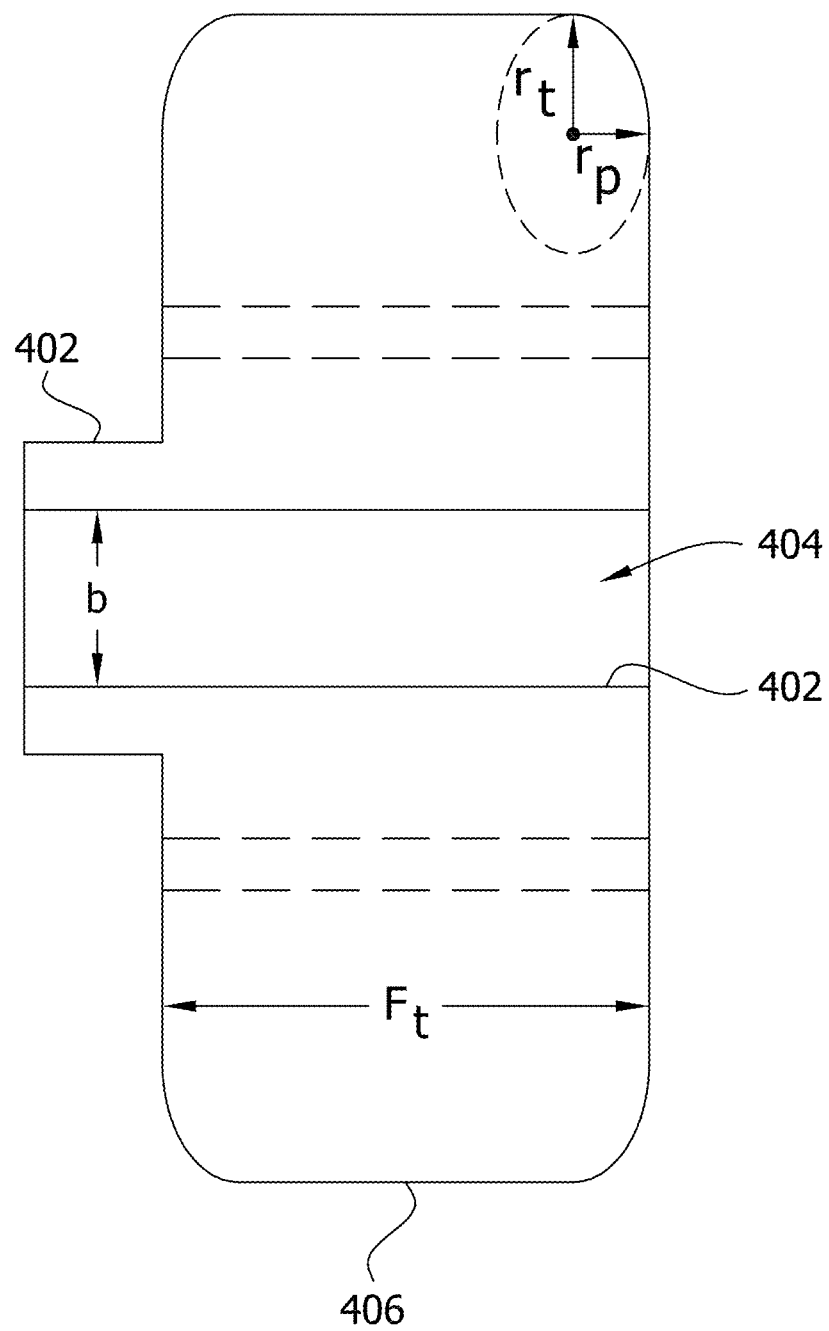
FIG. 5B and FIG. 5C are elevations of the finite flange of FIG. 4.
Figure 5C:
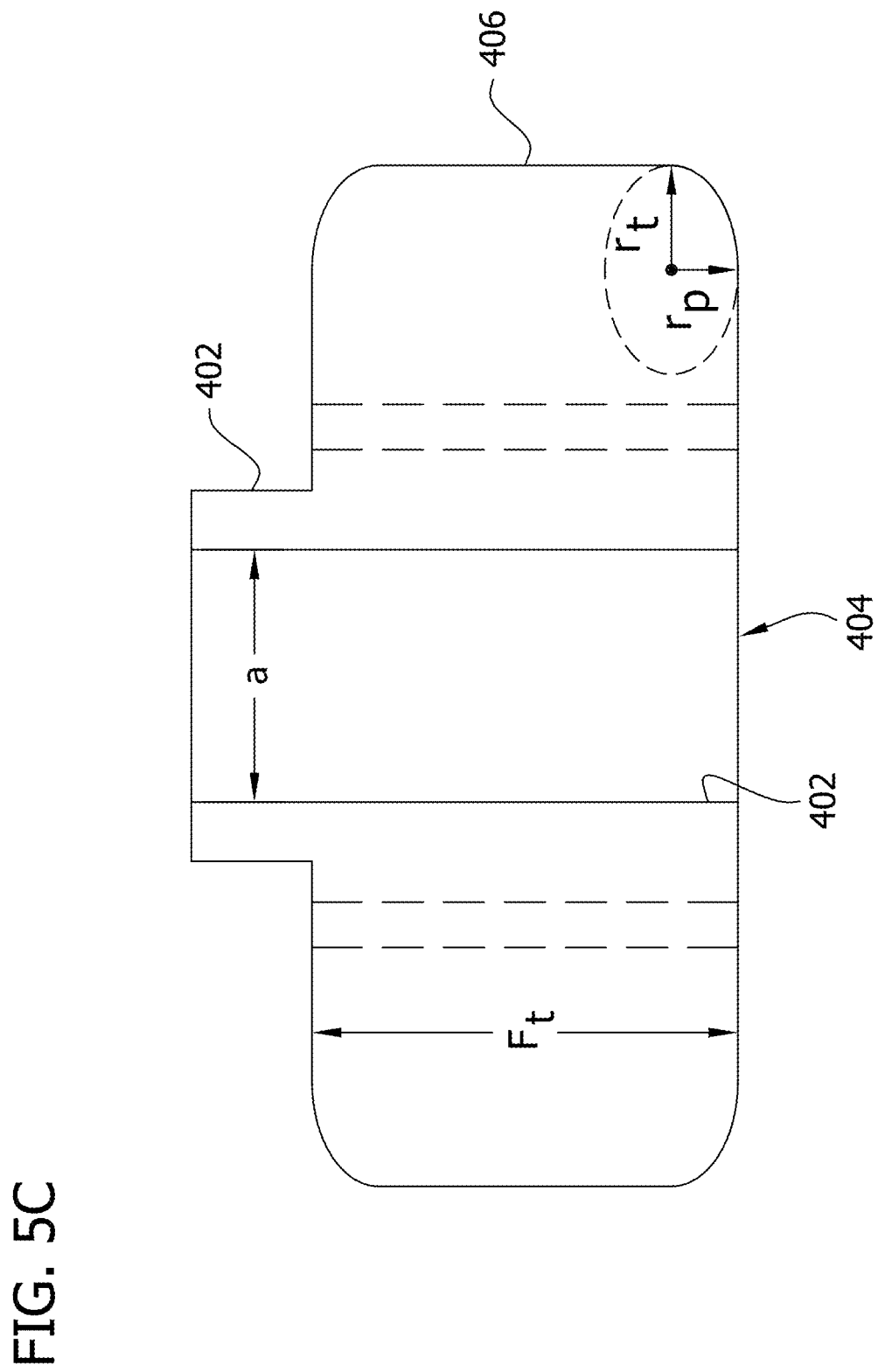

The general geometry of the waveguide probe 308 embodying aspects of the invention is shown in FIGS. 5A-5C. The flange 406 in the illustrated embodiment is generally rectangular in shape and generally planar adjacent aperture 404. And in an embodiment at least two opposing edge margins of flange 406 are advantageously curved to reduce the scattering at the edges of the flange. The curved edge margins of flange 406 are curved according to, for example, an exponential function. In another embodiment, the curved edge margins include rounded curves. In yet another embodiment, the curved edge margins include elliptical curves.

To reduce the scattering at the edges of the flange, flange 406 advantageously has one or more "smoothed" edge margins. The waveguide aperture dimensions are denoted by a and b, corresponding to the broad and narrow dimensions of the waveguide, respectively. The edge geometry of flange 406 differs from that of a conventional finite flange in this embodiment by replacing the standard right angle edges with a generally elliptical cross-section, with radii $r_t$ and $r_p$, providing a smoother geometrical transition at the edges. Radius, $r_t$, denotes the lateral directions that are transverse to the direction of wave propagation in the waveguide. Conversely, $r_p$ denotes a direction parallel to the direction of wave propagation.

This elliptically-tapered geometry illustrated in FIGS. 5A-5C significantly reduces unwanted reflections at the flange edges, as will be shown later. It is contemplated that the general geometries of the four edges on the front of the flange (plane of the aperture) and the four edges of the back of the flange (where the feeding waveguide meets the flange) may not be identical. Further, in the illustrated embodiment, all flange edges have identical radii. Dimensions $F_x$ (H-plane direction) and $F_y$ (E-plane direction) denote the footprint of the probe while $F_t$ represents the thickness of the flange. The location of the screw holes is compatible with that of a standard waveguide flange and fulfills the same functionality, such as connecting waveguides to each other and/or connecting to waveguide loads required for calibrating a vector network analyzer (VNA).

Figure 6:
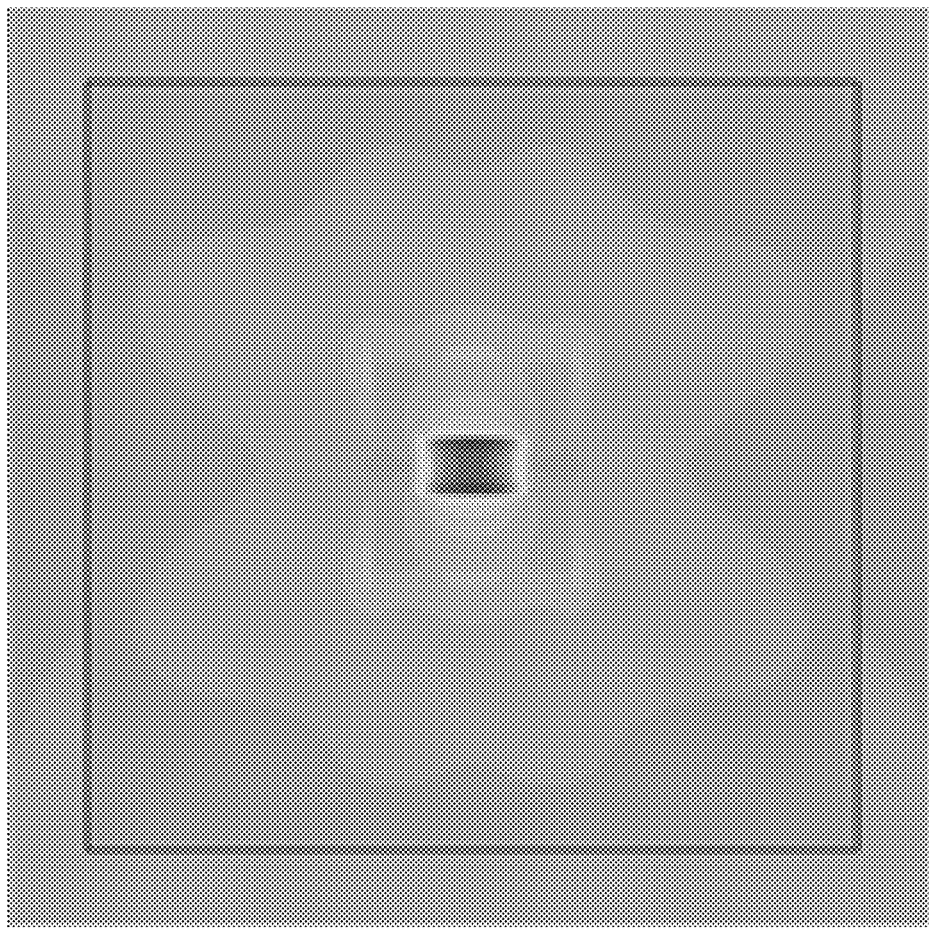
FIG. 6 illustrates exemplary electric field intensity inside a thin dielectric sheet into which the finite flange waveguide of FIG. 4 is radiating.

In an alternative embodiment, the edge margins of flange 406 are rounded. Exemplary smoothing includes different diameters of rounding the edges of flange 406. For example, the diameter of the rounded edges is from about 4 mm to about 20 mm. For comparison to FIG. 2, FIG. 6 illustrates exemplary electric field intensity inside a thin dielectric sheet into which the finite flange waveguide having rounded edges is radiating. The perturbation in the electric field distribution decreases as the diameter increases (e.g., the flange edge become smoother). Therefore, modifying the flange geometry to incorporate rounding, for example, the top and bottom edges of a conventional flange (e.g., flange 106) reduces errors.

Figure 7A:
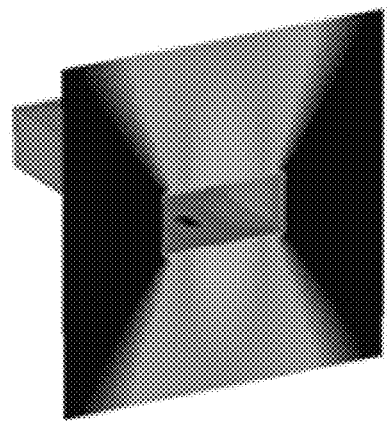
FIGS. 7A-7C illustrate exemplary surface current densities for an infinite flange, a conventional flange, and the flange of FIG. 4, respectively.
Figure 7B:
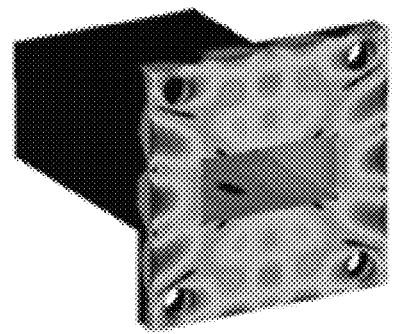
Figure 7C:
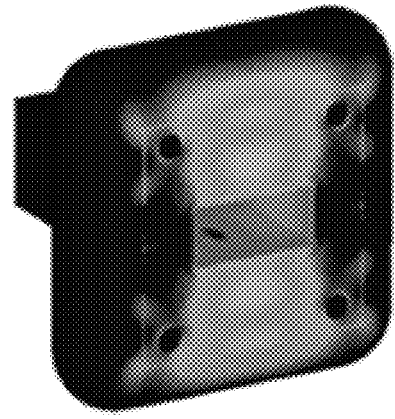

FIGS. 7A-7C illustrate exemplary surface current densities for an infinite flange waveguide, a standard waveguide (such as probe 100), and the waveguide of FIG. 4, respectively. The current densities in FIGS. 7A-7C are normalized to the same scale, providing a one-to-one comparison between the different geometries. The plots of surface current densities for an ideal infinite flange (FIG. 7A) are truncated so that they can be plotted with the same aperture size as the other flanges. For the infinite flange, the current density smoothly transitions away from the aperture. The current distribution is generally frequency independent with the exception that as the frequency increases the majority of the current becomes confined to a slightly narrower region on the flange. Also, the majority of the current flow (i.e., vertically in FIGS. 7A-7C) corresponds to the direction of the $TE_{10}$ (dominant waveguide mode) electric field polarization.

The surface current densities (see FIG. 7B) on the standard flange), such as flange 106, do not closely match those of the infinite flange. The pronounced variations in the current density distribution are due to the strong reflections generated by the discontinuity at the flange edges. A wave impedance mismatch between the fields directly in front of the flange and the surrounding environment causes this discontinuity resulting in a reflected wave. In addition, albeit to a lesser extent, the screw holes on the flange perturb the current density path as well. The coherent addition of the multiple reflected waves (from the flange edges and screw holes) creates an interference pattern that is unique for each frequency. In addition, maximum current density perturbations appear at all four edges. At the upper end of the frequency band the amplitude of the standing waves are reduced and are predominately in the direction of the $TE_{10}$ mode electric field polarization. This is due to the fact that the flange appears electrically larger (the operating wavelength is shorter) and, as was seen for the infinite flange case, the current distribution at higher frequencies tends to concentrate in a narrower region on the flange. Observation of the surface current density on the standard flange shows that the effects of the finite-sized flange are strongly dependent on the operating frequency.

For the sake of comparison, the surface current densities for the infinite flange waveguide and the waveguide of FIG. 4 as shown in FIG. 7A and FIG. 7C, respectively, are very similar indicating the improved results available from probe 308 in accordance with aspects of the present invention.

The effect of a standard flange edge, such as an edge of flange 106, is more prominent for a conductor-backed dielectric sheet or layered composites because the combination of the flange and the conductor backing of the sample creates a parallel plate transmission line guiding the electromagnetic wave to the edges of the flange. Advantageously, the curved flange edges embodying aspects of the invention significantly reduce the scattering of the electromagnetic waves because the discontinuity at the flange edges is significantly reduced, which also results in the reflections due to the flange edges to be reduced. As the curved flange edge diameter increases, the reflection coefficient more closely follows the ideal case. When using a theoretical model to recalculate dielectric characteristics, having a reflection coefficient that closely follows the ideal case is advantageous because the theoretical model that is used to estimate the material properties assumes an infinite flange, which assumes no reflected signal from the flange edge.

Figure 8:
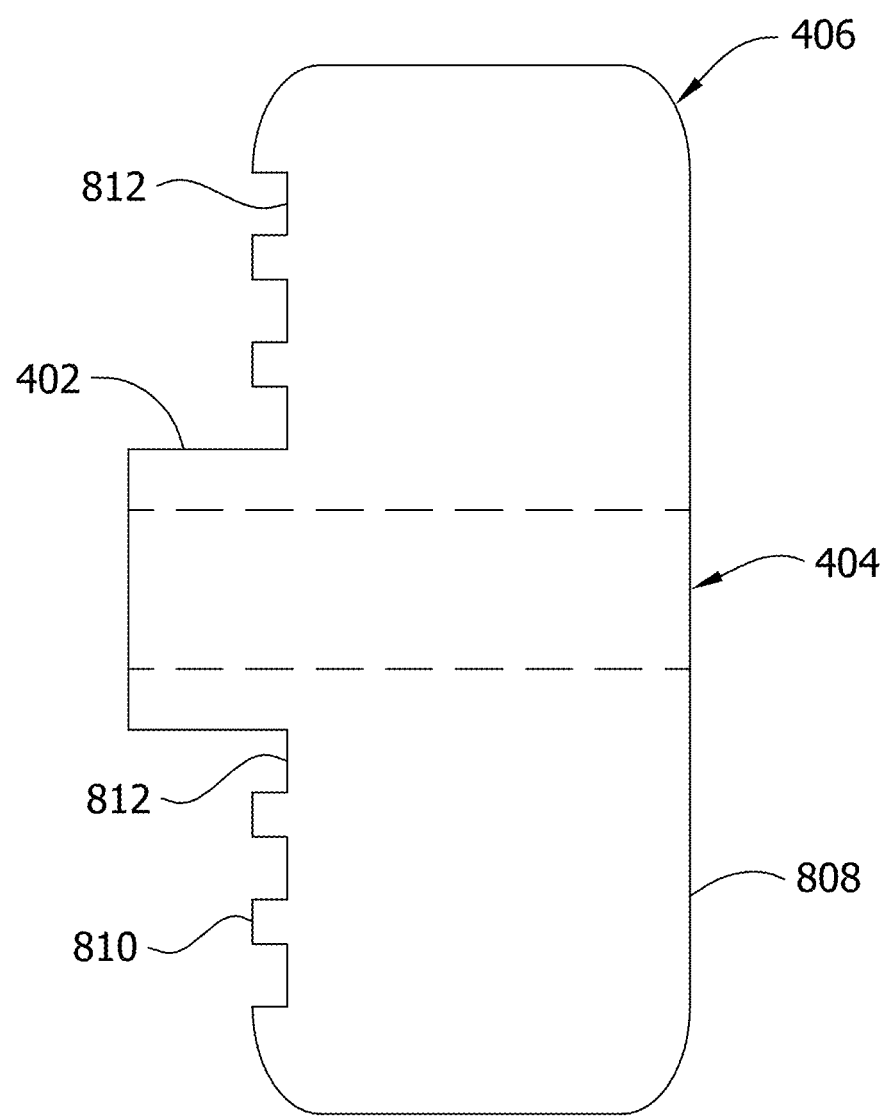
FIG. 8 illustrates an alternative embodiment of an open-ended waveguide for use in the test arrangement of FIG. 3.

Referring now to FIG. 8, in an embodiment, the flange 406 has a front surface 808 and a back surface 810. In this embodiment, the front surface 808 faces the object 310 when the electromagnetic signal is transmitted. This back surface 810 has surface variations for inhibiting unwanted electromagnetic energy from returning to the front surface 808 of flange 406. For example, back surface 810 has a plurality of grooves 812 (e.g., curved, rectangular, or V-shaped) formed therein. In another example, the surface variations include coatings, such as an absorbing material coating. The grooves or absorbing material coating may begin from the beginning of the curvature in the front face and extend to the back surface.

Figure 9A:
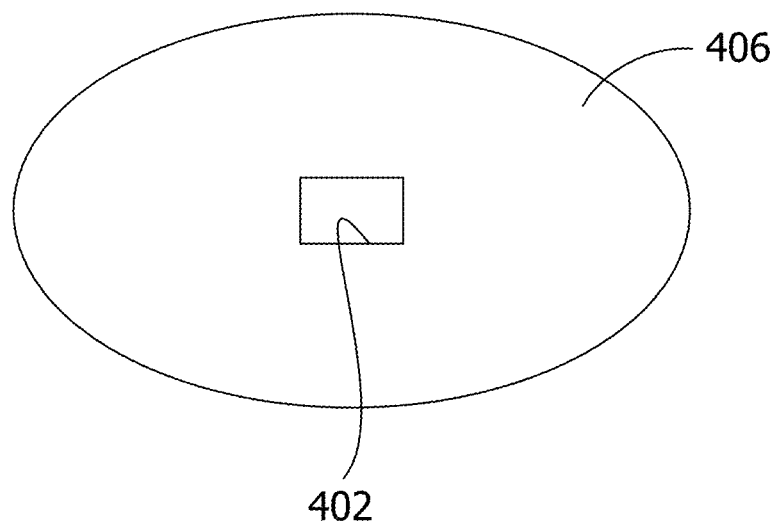
FIGS. 9A and 9B illustrate alternative embodiments of open-ended waveguides for use in the test arrangement of FIG. 3.
Figure 9B:
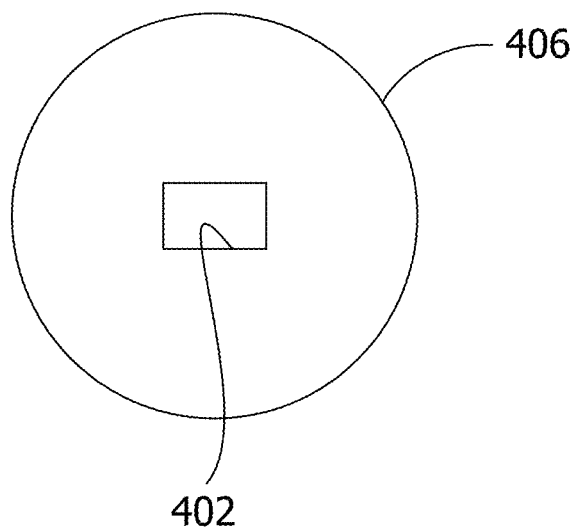

According to aspects of the invention, flange 406 can be planar or non-planar. Moreover, as shown in FIGS. 9A and 9B, embodiments of flange 406 are other shapes, such as elliptical and circular, respectively, in addition to the rectangular or square shapes described above.

In an aspect, a method of measuring a material characteristics of object 310 includes defining a flange geometry for an antenna, such as probe 308, as a function of the material characteristic to be measured and transmitting, by the antenna, an electromagnetic signal that includes microwave electromagnetic energy incident upon object 310. The method also includes receiving, by the antenna, an electromagnetic field reflected from object 310. The antenna has flange 406 extending outwardly therefrom and is shaped according to the defined flange geometry to reduce scattering, by one or more edges of the flange 406, of the electromagnetic field received by the antenna. Further, the method includes determining the material characteristic, such as a thickness, complex dielectric and complex permeability, based on the received electromagnetic field. In an embodiment, defining the flange geometry includes defining at least two opposing edge margins of flange 406 to be curved. Defining the flange geometry includes optimizing a radius of curvature of one or more edge margins of flange 406.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. An open-ended waveguide apparatus comprising:
a hollow guide structure and a signal source coupled thereto, said guide structure further having an open end defining an aperture through which an electromagnetic signal generated by the signal source is transmitted to an object located remotely from the aperture and through which an electromagnetic field reflected from the object is received by the aperture; and
a flange extending outwardly from the guide structure at the aperture, said flange having one or more continuously curved edge margins shaped to reduce undesired electromagnetic scattering from one or more edges of the flange and received by the aperture, wherein the guide structure is adapted for coupling to a receiver for sampling the reflected electromagnetic field received by the aperture, and wherein the receiver is adapted for coupling to a processor for determining at least one material characteristic of the object based on a sampled electromagnetic field reflected from the object.

2. The waveguide apparatus of claim 1, wherein the guide structure has a substantially rectangular cross-section.

3. The waveguide apparatus of claim 1, wherein the flange is generally rectangular in shape and generally planar from adjacent the aperture to adjacent the one or more continuously curved edge margins and extends generally transversely relative to the guide structure.

4. The waveguide apparatus of claim 3, wherein at least two opposing edge margins of the flange are continuously curved.

5. The waveguide apparatus of claim 3, wherein the continuously curved edge margins of the flange are curved according to an exponential function.

6. The waveguide apparatus of claim 3, wherein the continuously curved edge margins of the flange are rounded.

7. The waveguide apparatus of claim 3, wherein the one or more continuously curved edge margins configure the flange to function as an infinite flange.

8. The waveguide apparatus of claim 1, wherein the flange has a front surface and a back surface, said front surface facing the object when the electromagnetic signal is transmitted to the object, said back surface having surface variations for inhibiting unwanted electromagnetic energy from returning to the front surface of the flange.

9. The waveguide apparatus of claim 8, wherein the back surface of the flange has a plurality of grooves formed therein.

10. The waveguide apparatus of claim 1, wherein the flange comprises a conductive metal.

11. A method of measuring a material characteristic of an object comprising:
transmitting, by an antenna, an electromagnetic signal, said electromagnetic signal comprising microwave electromagnetic energy incident upon the object;

receiving, by the antenna, an electromagnetic field reflected from the object, said antenna having a flange extending outwardly therefrom, said flange having one or more smoothed edge margins shaped according to a defined flange geometry to reduce scattering, by the flange, of the electromagnetic field received by the antenna; and determining a material characteristic of the object based on the received electromagnetic field.

12. The method of claim 11, wherein the material characteristic comprises at least one of a thickness, a complex dielectric constant, and a complex permeability.

13. The method of claim 11, wherein the flange is generally rectangular in shape and generally planar adjacent the antenna, and wherein defining the flange geometry includes defining at least two opposing smoothed edge margins of the flange to be curved.

14. The method of claim 11, further comprising defining a flange geometry for the antenna as a function of the desired accuracy level for the material characteristic to be measured.

15. The method of claim 14, wherein defining the flange geometry comprises optimizing a radius of curvature of one or more smoothed edge margins of the flange.

16. A system for non-destructive testing comprising:
an open-ended waveguide having a signal source coupled thereto, said waveguide defining an aperture through which an electromagnetic signal generated by the signal source is transmitted to an object located remotely from the aperture and through which an electromagnetic field reflected from the object is received by the aperture;

a flange extending outwardly from the waveguide at the aperture, said flange having one or more continuously tapered edge margins to reduce electromagnetic field scattering from one or more edges of the flange and received by the aperture; and a processor configured to execute an estimation algorithm for determining at least one material characteristic of the object as a function of the reflected electromagnetic field received by the aperture.

17. The system of claim 16, wherein the material characteristic comprises at least one of a thickness, a complex dielectric constant, and a complex permeability.

18. The system of claim 16, wherein the signal source comprises an electric field source for illuminating the object, said electric field comprising electromagnetic energy having a frequency greater than ultra high frequency and being reflected by the object illuminated thereby.

19. The system of claim 16, wherein the electromagnetic signal generated by the signal source comprises microwave or millimeter wave electromagnetic energy.

20. The system of claim 16, wherein the flange is generally rectangular in shape and generally planar adjacent the aperture.

21. The system of claim 20, wherein at least two opposing continuously tapered edge margins of the flange are curved.

22. The system of claim 21, wherein the curved edge margins of the flange are rounded.

23. The system of claim 16, wherein the one or more continuously tapered edge margins configure the flange to function as an infinite flange.

24. The system of claim 16, wherein the flange comprises a conductive metal.

25. The system of claim 16, wherein the processor is configured to generate a multi-dimensional profile representative of the object as a function of the reflected electromagnetic field received by the aperture and further comprising a display operatively connected to the processor for displaying an image of the multi-dimensional profile generated thereby.

26. The system of claim 25, wherein the multi-dimensional profile comprises at least two of a complex dielectric constant of the object, a complex permeability of the object, and a thickness of the object.

* * * * *